(12) United States Patent
Duerig et al.

(10) Patent No.: US 6,287,329 B1
(45) Date of Patent: Sep. 11, 2001

(54) STENT KEEPER FOR A SELF-EXPANDING STENT DELIVERY SYSTEM

(75) Inventors: Thomas Duerig, Fremont; Dieter Stockel, Los Altos, both of CA (US)

(73) Assignee: Nitinol Development Corporation, Freemont, CA (US)

(*) Notice: Subject to any disclaimer, the term of this patent is extended or adjusted under 35 U.S.C. 154(b) by 0 days.

(21) Appl. No.: 09/340,573

(22) Filed: Jun. 28, 1999

(51) Int. Cl.[7] ........................................... A61F 2/06
(52) U.S. Cl. ............................... 623/1.11; 606/198
(58) Field of Search ............................... 606/191, 194, 606/195, 198, 200; 623/1.1, 1.11, 1.12, 12; 128/899

(56) References Cited

U.S. PATENT DOCUMENTS

| | | |
|---|---|---|
| 3,585,707 | 6/1971 | Stevens . |
| 4,580,568 | 4/1986 | Gianturco . |
| 4,665,771 | 5/1987 | Mitchell . |
| 4,665,905 | 5/1987 | Brown . |
| 4,733,665 | 3/1988 | Palmaz . |
| 4,925,445 | 5/1990 | Sakamoto . |
| 5,045,072 | 9/1991 | Castillo . |
| 5,254,107 | 10/1993 | Soltesz . |
| 5,433,723 * | 7/1995 | Linderberg et al. ............... 623/1.12 |
| 5,662,703 * | 9/1997 | Yurek et al. ...................... 623/1.12 |
| 5,733,267 * | 3/1998 | Del Toro ........................... 623/1.11 |
| 5,800,517 * | 9/1998 | Anderson et al. ................ 623/1.12 |
| 6,001,123 * | 12/1999 | Lau ..................................... 623/1.12 |

* cited by examiner

Primary Examiner—Henry J. Recla
Assistant Examiner—William W. Lewis

(57) ABSTRACT

A delivery apparatus including an outer sheath, made from an elongated tubular member having distal and proximal ends. The apparatus further includes a self-expanding stent located within the distal end of the sheath along a load area. The stent makes frictional contact with the inner layer of said sheath. Lastly, the apparatus includes a readily removable member or keeper, which is disposed along the outer sheath along at least a portion of the load area. The member has sufficient rigidity to prevent the outer sheath from expanding along the load area prior to delivery of the stent.

15 Claims, 6 Drawing Sheets

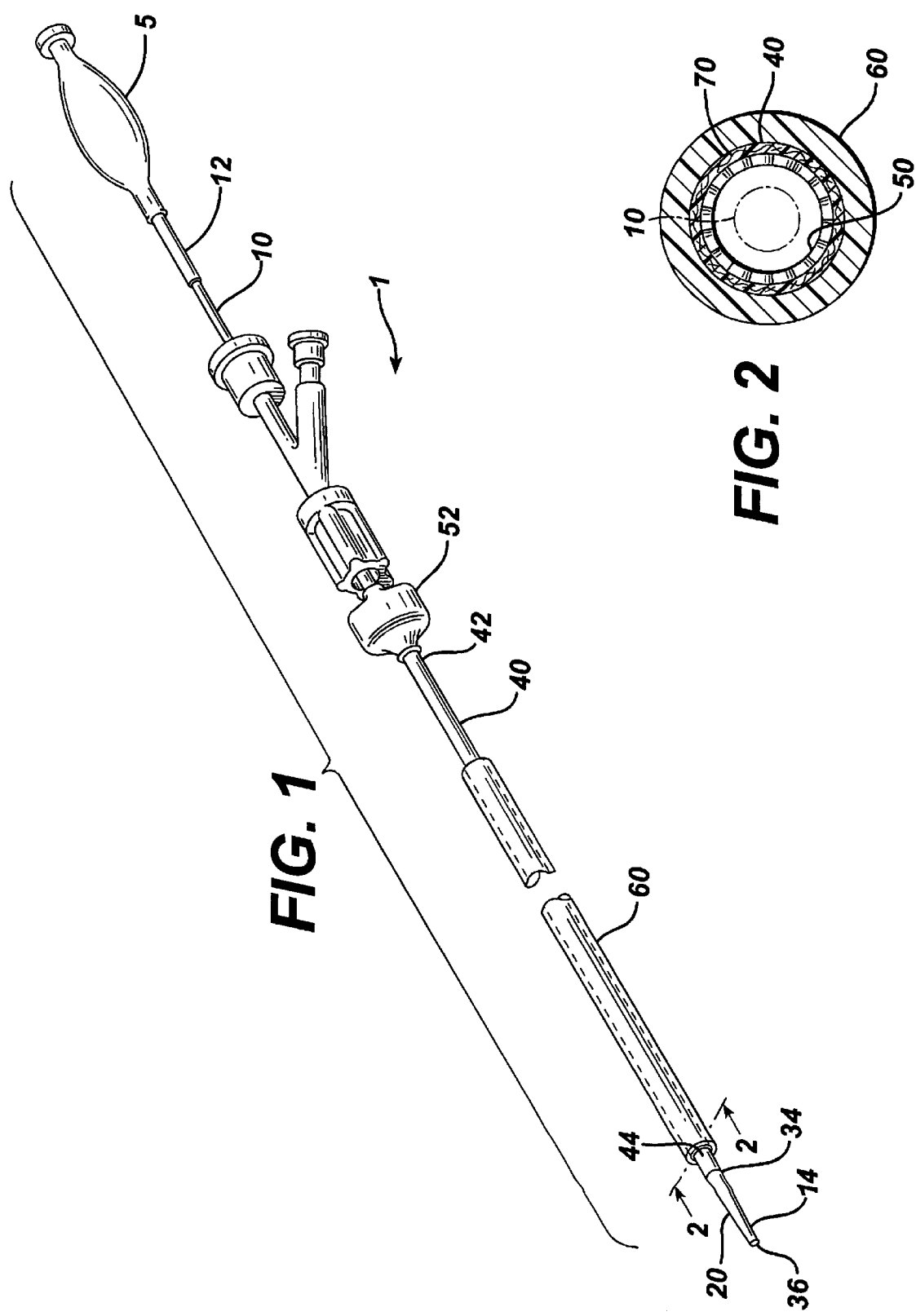

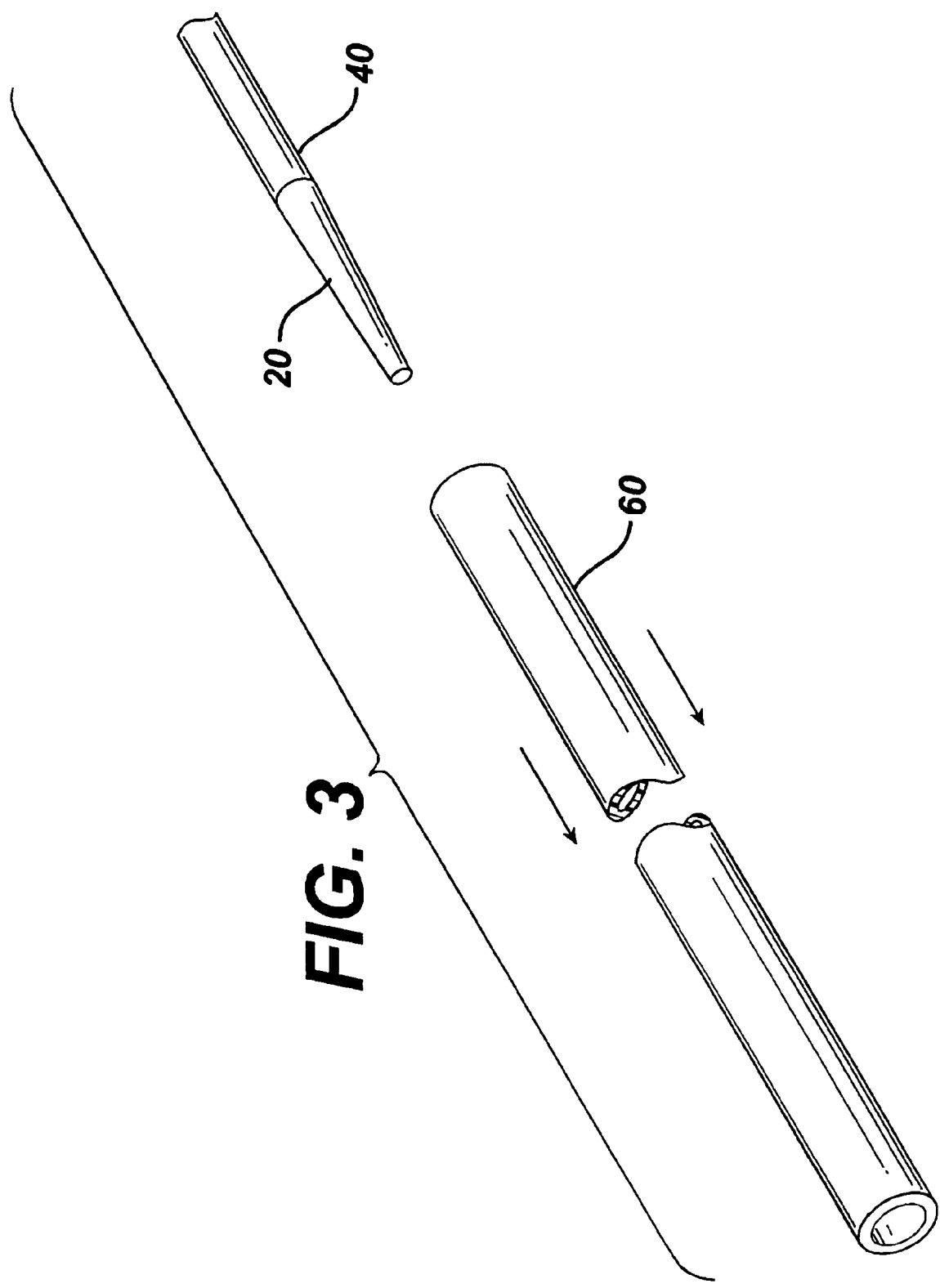

STENT KEEPER FOR A SELF-EXPANDING STENT DELIVERY SYSTEM

FIELD OF THE INVENTION

The present invention relates to self-expanding intraluminal grafts ("stents") for use within a body passageway or duct which are particularly useful for repairing blood vessels narrowed or occluded by disease. The present invention relates even further to systems for delivering such stents.

BACKGROUND OF THE INVENTION

Percutaneous transluminal coronary angioplasty (PTCA) is a therapeutic medical procedure used to increase blood flow through the coronary artery and can often be used as an alternative to coronary by-pass surgery. In this procedure, the angioplasty balloon is inflated within the stenosed vessel, or body passageway, in order to shear and disrupt the wall components of the vessel to obtain an enlarged lumen. With respect to arterial stenosed lesions, the relatively incompressible plaque remains unaltered, while the more elastic medial and adventitial layers of the body passageway stretch around the plaque. This process produces dissection, or a splitting and tearing, of the body passageway wall layers, wherein the intima, or internal surface of the artery or body passageway, suffers fissuring. This dissection forms a "flap" of underlying tissue which may reduce the blood flow through the lumen, or block the lumen. Typically, the distending intraluminal pressure within the body passageway can hold the disrupted layer, or flap, in place. If the intimal flap created by the balloon dilation procedure is not maintained in place against the expanded intima, the intimal flap can fold down into the lumen and close off the lumen, or may even become detached and enter the body passageway. When the intimal flap closes off the body passageway, immediate surgery is necessary to correct this problem.

Recently, transluminal prostheses have been widely used in the medical arts for implantation in blood vessels, biliary ducts, or other similar organs of the living body. These prostheses are commonly known as stents and are used to maintain, open, or dilate tubular structures. An example of a commonly used stent is given in U.S. Pat. No. 4,733,665 filed by Palmaz on Nov. 7, 1985, which is hereby incorporated herein by reference. Such stents are often referred to as balloon expandable stents. Typically the stent is made from a solid tube of stainless steel. Thereafter, a series of cuts are made in the wall of the stent. The stent has a first smaller diameter which permits the stent to be delivered through the human vasculature by being crimped onto a balloon catheter. The stent also has a second, expanded diameter, upon the application, by the balloon catheter, from the interior of the tubular shaped member of a radially, outwardly extending force.

However, such stents are often impractical for use in some vessels such as the carotid artery. The carotid artery is easily accessible from the exterior of the human body, and is often visible by looking at ones neck. A patient having a balloon expandable stent made from stainless steel or the like, placed in their carotid artery might be susceptible to sever injury through day to day activity. A sufficient force placed on the patients neck, such as by falling, could cause the stent to collapse, resulting in injury to the patient. In order to prevent this and to address other shortcomings of balloon expandable stents, self expanding stents were developed. Self expanding stents act like springs and will recover to their expanded or implanted configuration after being crushed.

One type of self-expanding stent is disclosed in U.S. Pat. No. 4,665,771, which stent has a radially and axially flexible, elastic tubular body with a predetermined diameter that is variable under axial movement of ends of the body relative to each other and which is composed of a plurality of individually rigid but flexible and elastic thread elements defining a radially self-expanding helix. This type of stent is known in the art as a "braided stent" and is so designated herein. Placement of such stents in a body vessel can be achieved by a device which comprises an outer catheter for holding the stent at its distal end, and an inner piston which pushes the stent forward once it is in position.

Other types of self-expanding stents use alloys such as Nitinol (Ni—Ti alloy) which have shape memory and/or superelastic characteristics in medical devices which are designed to be inserted into a patient's body. The shape memory characteristics allow the devices to be deformed to facilitate their insertion into a body lumen or cavity and then be heated within the body so that the device returns to its original shape. Superelastic characteristics on the other hand generally allow the metal to be deformed and restrained in the deformed condition to facilitate the insertion of the medical device containing the metal into a patient's body, with such deformation causing the phase transformation. Once within the body lumen the restraint on the superelastic member can be removed, thereby reducing the stress therein so that the superelastic member can return to its original un-deformed shape by the transformation back to the original phase.

Alloys having shape memory/superelastic characteristics generally have at least two phases. These phases are a martensite phase, which has a relatively low tensile strength and which is stable at relatively low temperatures, and an austenite phase, which has a relatively high tensile strength and which is stable at temperatures higher than the martensite phase.

When stress is applied to a specimen of a metal such as Nitinol exhibiting superelastic characteristics at a temperature above which the austenite is stable (i.e. the temperature at which the transformation of martensite phase to the austenite phase is complete), the specimen deforms elastically until it reaches a particular stress level where the alloy then undergoes a stress-induced phase transformation from the austenite phase to the martensite phase. As the phase transformation proceeds, the alloy undergoes significant increases in strain but with little or no corresponding increases in stress. The strain increases while the stress remains essentially constant until the transformation of the austenite phase to the martensite phase is complete. Thereafter, further increase in stress are necessary to cause further deformation. The martensitic metal first deforms elastically upon the application of additional stress and then plastically with permanent residual deformation.

If the load on the specimen is removed before any permanent deformation has occurred, the martensitic specimen will elastically recover and transform back to the austenite phase. The reduction in stress first causes a decrease in strain. As stress reduction reaches the level at which the martensite phase transforms back into the austenite phase, the stress level in the specimen will remain essentially constant (but substantially less than the constant stress level at which the austenite transforms to the martensite) until the transformation back to the austenite phase is complete, i.e. there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as superelasticity or pseudoelasticity. It is this property of the material which makes it useful in manufacturing tube cut self-expanding stents. The prior art makes reference to the use of metal alloys having superelastic characteristics in medical devices which are intended to be inserted or otherwise used within a patient's body. See for example, U.S. Pat. No. 4,665,905 (Jervis) and U.S. Pat. No. 4,925,445 (Sakamoto et al.).

Designing delivery systems for delivering self-expanding stents has proven difficult. One example of a prior art self-expanding stent delivery system is shown in U.S. Pat. No. 4,580,568 issued to Gianturco on Apr. 8, 1986. This reference discloses a delivery apparatus which uses a hollow sheath, like a catheter. The sheath is inserted into a body vessel and navigated therethrough so that its distal end is adjacent the target site. The stent is then compressed to a smaller diameter and load into the sheath at the sheath's proximal end. A cylindrical flat end pusher, having a diameter almost equal to the inside diameter of the sheath is inserted into the sheath behind the stent. The pusher is then used to push the stent from the proximal end of the sheath to the distal end of the sheath. Once the stent is at the distal end of the sheath, the sheath is pulled back, while the pusher remain stationary, thereby exposing the stent and expanding it within the vessel.

However, delivering the stent through the entire length of the catheter can cause many problems, including possible damage to a vessel or the stent during its travel. In addition, it is often difficult to design a pusher having enough flexibility to navigate through the catheter, but also enough stiffness to push the stent out of the catheter. Therefore, it was discovered that pre-loading the stent into the distal and of the catheter, and then delivering the catheter through the vessel to the target site may be a better approach. In order to ensure proper placement of the stent within catheter, it is often preferred that the stent be pre-load at the manufacturing 'site. Except this in itself has posed some problems. Because the catheter exerts a significant force on the self expanding stent, the stent may tend to become imbedded within the inner wall of the catheter. When this happens, the catheter has difficulty sliding over the stent during delivery. This situation can result in the stent becoming stuck inside the catheter, or could damage the stent during delivery. If the catheter is not exerting enough force on the stent, the stent could cause the outer sheath to bulge outwardly, which can also result in delivery problems. While stronger materials could be used to constrain the stent, such a solution would interfere with the flexibility of the delivery system, which is a primary design consideration.

Therefore, there has been a need for a self-expanding stent delivery system which overcomes the above referenced problems associated with prior art delivery systems. Specifically, there has been a need for a self-expanding stent delivery system wherein the stent is loaded at the distal end of a catheter and wherein the catheter effectively resists the stent from imbedding itself therein. The present invention provides such a device.

SUMMARY OF THE INVENTION

In accordance with the present invention, there is provided a delivery apparatus for a self-expanding stent. The apparatus includes an outer sheath, made from an elongated tubular member having distal and proximal ends. The apparatus further includes a self-expanding stent located within the distal end of the sheath along a load area. The stent makes frictional contact with the inner layer of the sheath. The apparatus also includes a readily removable member or keeper, which is disposed along the outer sheath along at least a portion of the load area. The member has sufficient rigidity to prevent the outer sheath from expanding along the load area prior to delivery of the stent.

BRIEF DESCRIPTION OF DRAWINGS

The foregoing and other aspects of the present invention will best be appreciated with reference to the detailed description of the invention in conjunction with the accompanying drawings, wherein:

FIG. 1 is a perspective view of a stent delivery apparatus made in accordance with the present invention.

FIG. 2 is a cross section of the device shown in FIG. 1, taken along lines 2—2.

FIG. 3 is a perspective view of a device made in accordance with the present invention, wherein the rigid member or keeper has been removed from the distal end of the sheath.

DETAILED DESCRIPTION OF THE INVENTION

Figure 4:
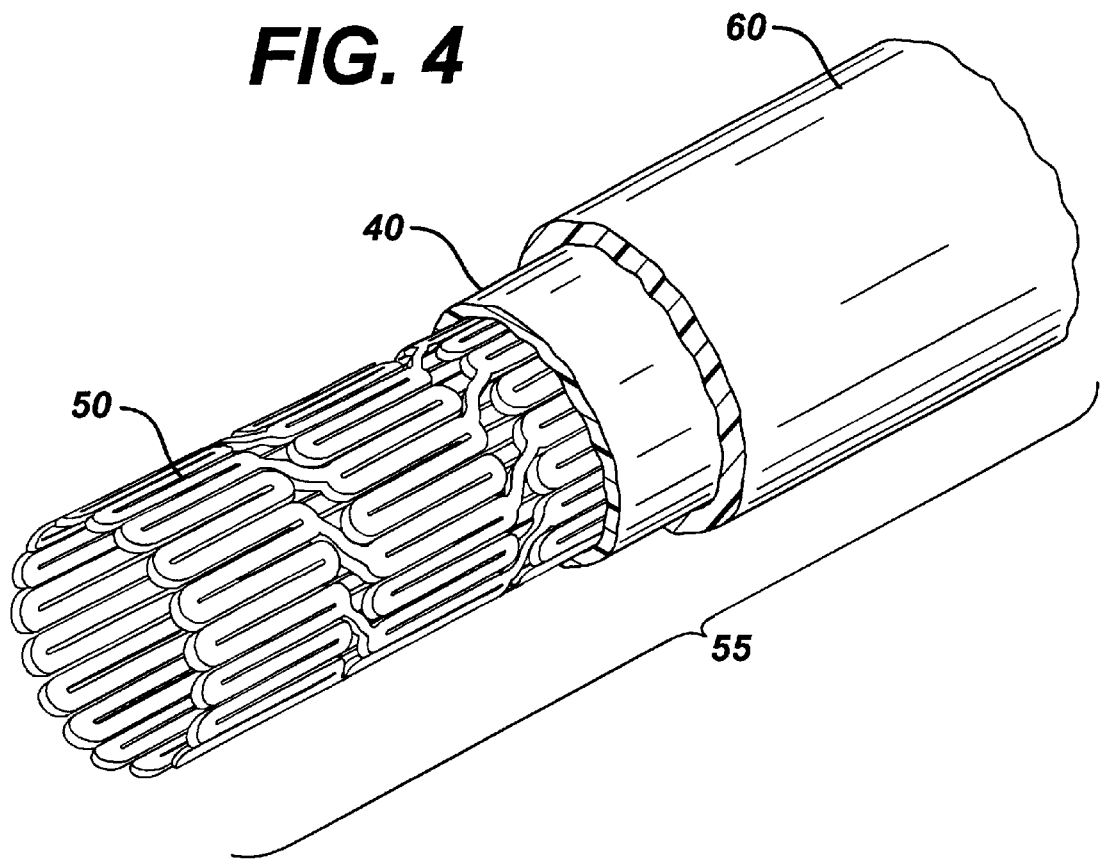
FIG. 4 is a simplified view of the distal end of the apparatus shown in FIG. 1, wherein various layers have been cut away to show different components of the apparatus.

Referring now to the figures wherein like numerals indicate the same element throughout the views, there is shown in FIGS. 1 and 2 a self-expanding stent delivery apparatus 1 made in accordance with the present invention. Apparatus 1 is similar to the stent delivery apparatus described in commonly assigned U.S. patent applications Ser. No. 09/042,276 filed on Mar. 13, 1998 U.S. Pat No. 6,019,778 and Ser. No. 09/243,750 filed on Feb. 3, 1999, pending the disclosures of both being hereby incorporated herein by reference. Apparatus 1 comprises inner and outer coaxial tubes. The inner tube is called the shaft 10 and the outer tube is called the sheath 40. Shaft 10 has proximal and distal ends 12 and 14 respectively. The proximal end 12 of the shaft has a luer lock hub 5 attached thereto. Shaft 10 has a proximal portion which is preferably made from a relatively stiff material such as stainless steel or Nitinol and a distal portion which is preferably made from a more flexible material such as a polymer.

The distal portion 14 of the shaft 10 has a distal tip 20 attached thereto. Distal tip 20 can be made from any number of materials known in the art including polyamide, polyurethane, polytetrafluoroethylene, and polyethylene including multi-layer or single layer structures. The distal tip 20 has a proximal end 34 whose diameter is substantially the same as the outer diameter of the sheath 40. The distal tip tapers to a smaller diameter from its proximal end 34 to its distal end 36, wherein the distal end 36 of the distal tip has a diameter smaller than the inner diameter of the sheath. Tip 20 helps to prevent blood from entering the sheath 40 as the apparatus 1 is being navigated through the body vessels. As will be discussed later herein, attached to distal portion 14 of shaft 10 is a stop which is proximal to the distal tip 20 and stent 50. Preferably, the diameter of stop is large enough to make sufficient contact with the stent (FIG. 4) without making frictional contact with the inner layer of the outer sheath 40. As will be explained later herein, the stop helps to push the stent out of the sheath during deployment, by preventing the stent from migrating proximally within the sheath 40 during retraction for stent deployment. During deployment, the outer sheath 40 is moved in a proximal direction relative to the stationary inner shaft 10.

Sheath 40 is preferably a polymeric catheter and has a proximal end 42 terminating at a Luer hub 52. Sheath 40 also has a distal end 44 which terminates at the proximal end 34 of distal tip 20 of the shaft 10, when the stent 50 is in its fully un-deployed position as shown in the figures. Sheath 40 preferably comprises an outer polymer layer, preferably nylon, and an inner polymer layer, preferably polytetrafluroethylene. Other suitable polymers for the inner and outer layers include any suitable material known to those skilled in the art including polyethylene or polyamide. Positioned between outer and inner layers is a wire reinforcing layer which is preferably a braided wire. Braided reinforcing layer 70 is preferably made from stainless steel. The use of braiding reinforcing layers in other types of medical devices can be found in U.S. Pat. No. 3,585,707 issued to Stevens on Jun. 22, 1971, U.S. Pat. No. 5,045,072 issued to Castillo et al. on Sep. 3, 1991, and U.S. Pat. No. 5,254,107 issued to Soltesz on Oct. 19, 1993, all of which are hereby incorporated herein by reference.

As seen from the FIGS. 2 and 4 the apparatus further includes a self-expanding stent 50 located within the distal end of the sheath along what is called a load area 55. The stent makes frictional contact with the inner layer of said sheath along the load area 55. Self-expanding stent 50 can take on any number of designs known to those skilled in the art, some of which were described above. As seen from FIG. 4, stent 50 is preferably is formed from a tube having slots or the like cut therein by laser cutting. Stent 50 has a first smaller diameter for insertion into the vessel, as shown in the figures, and a second larger diameter for deployment into the vessel (not shown). The tubular member includes a plurality of adjacent hoops extending between the front and back ends. The hoops are made from a plurality of longitudinal struts and a plurality of loops connecting adjacent struts. The member further includes a plurality of bridges connecting adjacent hoops to one another.

In addition, stent 50 is preferably made from an alloy comprising from about 50.5% (as used herein these percentages refer to atomic percentages) Ni to about 60% Ni, and most preferably about 55% Ni, with the remainder of the alloy Ti. Preferably, the stent is such that it is superelastic at body temperature, and preferably has an Af in the range from about 24° C. to about 37° C. The superelastic design of the stent makes it crush recoverable which, as discussed above, can be used as a stent or frame for any number of vascular devices for different applications.

In accordance with the present invention, apparatus 1 further includes a readily removable rigid member or keeper 60. Member 60 is disposed along the outer sheath along at least a portion of the load area 55. The member has sufficient rigidity and creep resistance to prevent the outer sheath from expanding along the load area prior to delivery of the stent. Member 60 can be made from any number of materials known to those skilled in the art including high density polyethylene, nitinol, stainless steel, PET.

Member 60 substantially prevents the sheath 40 from expanding along the load area 55 where the stent 50 is exerting an outward force thereon. As mentioned earlier, if the sheath expands too much it can increase its outside diameter enough to make it substantially useless for insertion into certain smaller vessels. In addition, member 60 also helps keep the stent from imbedding itself into the inner surface of sheath 40. That is because the sheath 40 is constrained from expanding by member 60, it becomes more rigid itself, and therefore helps better prevent imbedment of the stent 50. Imbedding of the stent into the delivery system is the sum of two factors, pooch (or sagging) and indentation. Indentation is where a strut of the stent indents into the material such that its outer face and both of its sides are at least partially surrounded by the delivery system material. Pooch is where the outward force of the stent causes the delivery system material to sag in-between adjacent struts. The pooch effect is more pronounced with more flexible, less rigid materials. Member 60 helps to reduce the pooch effect by effectively making the distal end of the delivery device more rigid and giving less room for the stent to move outwardly. In addition, because the member 60 is so rigid, sheath 40 can now be made from a more flexible material. A more flexible sheath 40 preferably causes better tracking. In addition, the sheath could be made thinner, causing the profile, or outer diameter, to decrease. By reducing the profile of the outer sheath, the number of potential vessels that the device can be deployed in increases because it can now reach smaller vessels.

As seen from FIG. 3, it is preferred that member 60 be readily removable from the outer sheath 40. For the embodiment shown in FIG. 3, member 60 would simply manually slide right off, prior to deployment of the apparatus within a patient. However, many other methods known to those skilled in the art could be used for making the stent readily removable. For example, one or more score lines could be placed down the length of the member 60 in order to peel the stent off. In addition, the member could be a helical wrap around the outside of the sheath which is unwrapped to remove.

Figure 5:
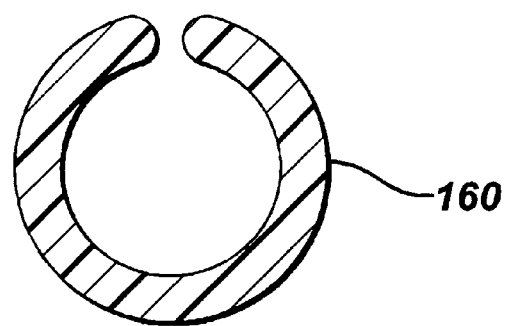
FIGS. 5–7 are cross-sectional views of different embodiments of a stent keeper made in accordance with the present invention.
Figure 6:
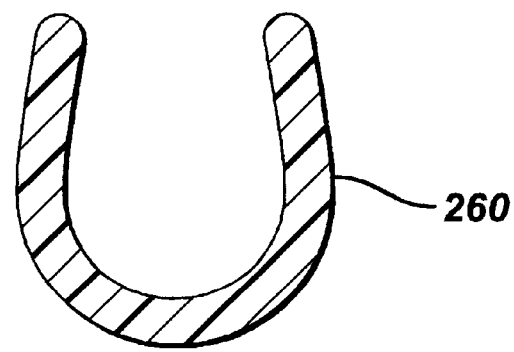
Figure 7:
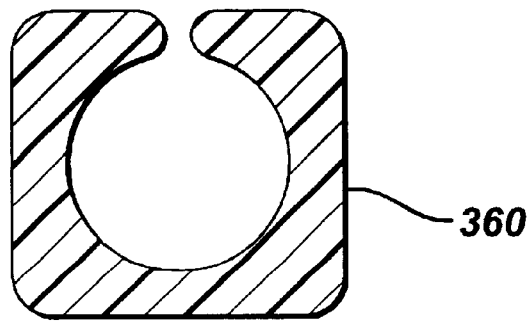
Figure 8:
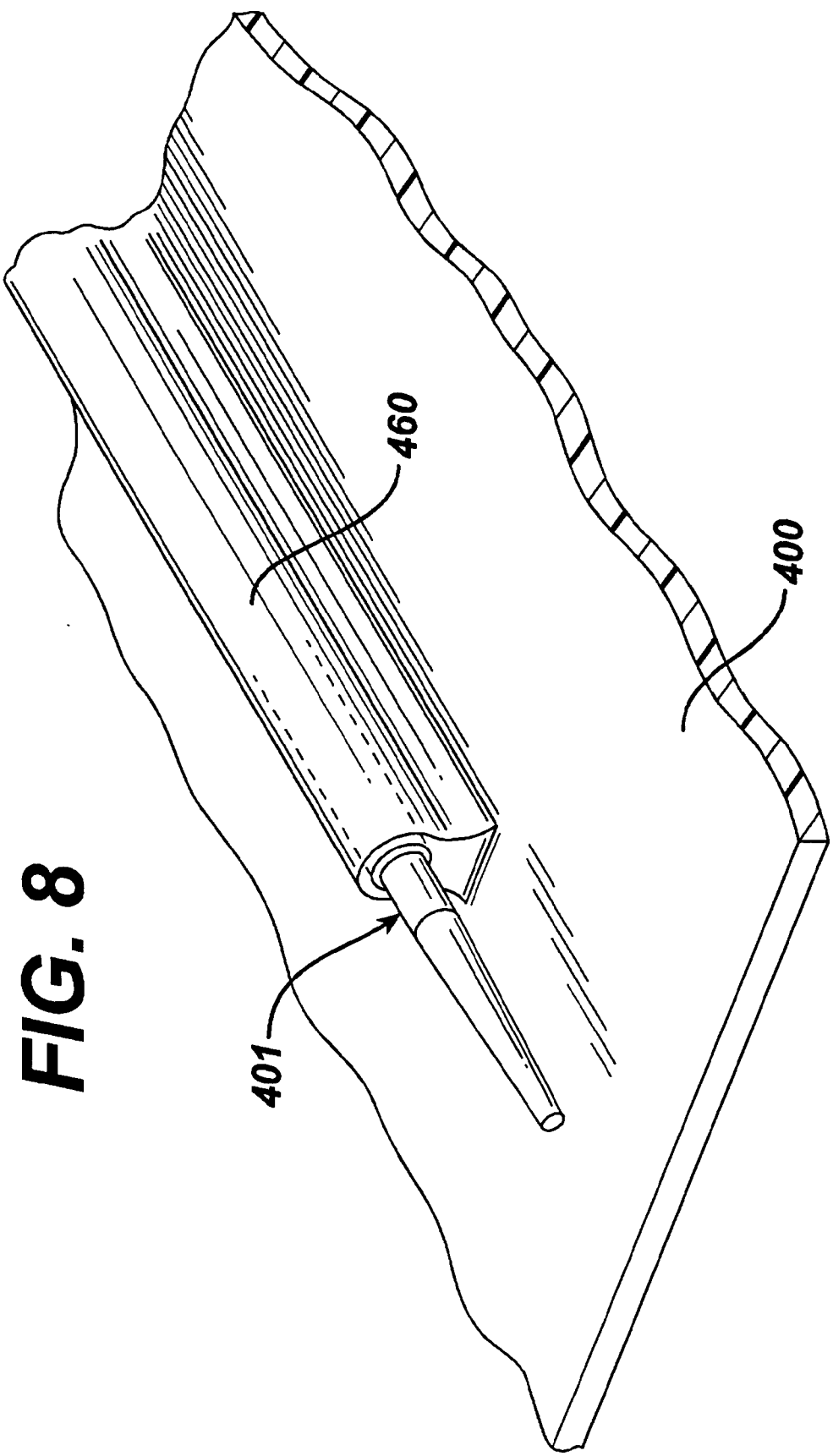
FIG. 8 is a simplified perspective view of an alternative embodiment of the present invention.

While FIGS. 1–4 show the member as being a tubular member, many other embodiments are also possible. FIGS. 5, 6 and 7 show different cross sections of different shaped members. FIG. 5 shows a C-shaped member 160, FIG. 6 shows a U-shaped member 260, and FIG. 7 shows a block C-shaped member 360. Another preferred embodiment is shown in FIG. 8. In that figure, member 460 is actually incorporated into part of the packaging 400. Packaging 400 could be a long thin sheet of material, such as paperboard or plastic, onto which the apparatus 401 is attached. A member 460 is attached or integral to the packaging and helps attach 401 to 400. The package 400 and apparatus 401 can then be covered with a clear polymer or the like.

Figure 9:
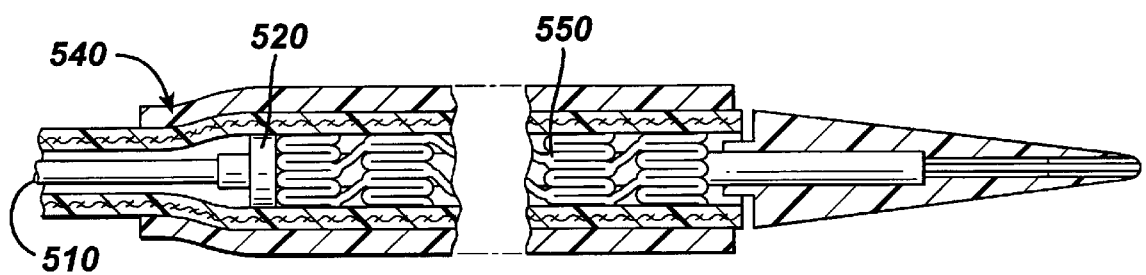
FIG. 9 is a simplified cross sectional view of yet another alternative embodiment of the present invention.

FIG. 9 shows a cross-sectional view of an additional embodiment of an apparatus 501 made in accordance with the present invention. Apparatus 501 is very similar to apparatus 1. The apparatus has an outer sheath 540. However, outer sheath 540 has an enlarged section 542 adjacent its distal end. The enlarged section has a greater inside and outside diameter than the inside and outside diameter of the sheath proximal to the enlarged section. The apparatus also includes an inner shaft 510 located coaxially within the outer sheath. In addition, the apparatus includes a self-expanding stent 550 located within the enlarged section of the outer sheath. The reduction in the size of the outer diameter of sheath 540 proximal to enlarged section 542 results in an increase in the clearance between the delivery device and a guiding catheter which helps deliver apparatus of this type. Using fluoroscopy, the physician will view an image of the target site within the vessel, before and after deployment of the stent, by injecting a radiopaque solution through the guiding catheter with the apparatus 501 inside. Because the clearance between the outer sheath 40, and the guiding catheter is increased by tapering or reducing the outer diameter of the sheath proximal to section 542, higher injection rates are achieved, resulting in better images of the target site for the physician. The tapering of sheath 40 provides higher injection rates of radiopaque fluid, both before and after deployment of the stent.

FIG. 9 also shows the stop 520 on shaft 510. Shaft 10 has a similar stop but was not shown in the prior figures. During deployment of the stent, the sheath and shaft are locked together at their proximal ends by a Tuohy Borst valve. This prevents any sliding movement between the shaft and sheath which could result in a premature deployment or partial deployment of the stent. When the stent reaches its target site and is ready for deployment, the Tuohy Borst valve is opened so that the sheath and shaft are no longer locked together. Thereafter, the sheath is slid back (or the shaft pushed forward) and pusher 520 makes sufficient contact with the stent 550 so that as the sheath is pulled back, the stent is exposed and expands to fill and make contact with the target vessel.

Although particular embodiments of the present invention have been shown and described, modification may be made to the device and/or method without departing from the spirit and scope of the present invention. The terms used in describing the invention are used in their descriptive sense and not as terms of limitations.

That which is claimed is:

1. A delivery apparatus for a self-expanding stent, said apparatus comprising:
   a) an outer sheath, comprising an elongated tubular member having distal and proximal ends;
   b) a self-expanding stent located within said distal end of said outer sheath along a load area, said self-expanding stent making frictional contact with an inner layer of said outer sheath; and
   c) a readily removable member disposed along said outer sheath along at least a portion of said load area, said readily removable member having a semi-tubular configuration with a substantially C-shaped cross section and having sufficient rigidity to substantially prevent said outer sheath from expanding along said load area prior to delivery of said self-expanding stent.

2. The apparatus according to claim 1 wherein said readily removable member is made from materials selected from the group comprising: polyethylene, nickel-titanium alloy, stainless steel.

3. The apparatus according to claim 1, further including a package enclosing said apparatus for storing and shipping said apparatus, and wherein said readily removable member is attached to said package.

4. The apparatus of claim 1 wherein said stent is made from a superelastic nickel-titanium alloy.

5. A delivery apparatus for a self-expanding stent, said apparatus comprising:
   a) an outer sheath, comprising an elongated tubular member having distal and proximal ends, an inner shaft located coaxially within said outer sheath, said inner shaft having a distal end, extending distal to said distal end of said outer sheath, and a proximal end, extending proximal to said proximal end of said outer sheath, said inner shaft further including a stop attached thereto, said stop being proximal to said distal end of said outer sheath;
   b) a self-expanding stent located within said outer sheath, said self-expanding stent making frictional contact with an inner layer of said outer sheath along a load area, said load area located between said stop and said distal end of said outer sheath with a portion of said inner shaft disposed coaxially within a lumen of said self-expanding stent; and
   c) a readily removable member disposed along said outer sheath along at least a portion of said load area, said readily removable member having a semi-tubular configuration with a substantially C-shaped cross section and having sufficient rigidity to substantially prevent said outer sheath from expanding along said load area prior to delivery of said self-expanding stent.

6. The apparatus according to claim 5 wherein said readily removable member is made from materials selected from the group comprising: polyethylene, nickel-titanium alloy, stainless steel.

7. The apparatus according to claim 5, further including a package enclosing said apparatus for storing and shipping said apparatus, and wherein said readily removable member is attached to said package.

8. The apparatus of claim 5 wherein said stent is made from a superelastic nickel-titanium alloy.

9. The apparatus according to claim 5 wherein said readily removable member comprises a semi-tubular shaped member having a U-shaped cross-section which slides on and off said sheath.

10. The apparatus according to claim 5, further including a package enclosing said apparatus for storing and shipping said apparatus, and wherein said readily removable member is attached to said package.

11. The apparatus of claim 5 wherein said stent is made from a superelastic nickel-titanium alloy.

12. A delivery apparatus for a self-expanding stent, said apparatus comprising:
   a) an outer sheath, comprising an elongated tubular member having distal and proximal ends;
   b) a self-expanding stent located within said distal end of said outer sheath along a load area, said self-expanding stent making frictional contact with an inner layer of said outer sheath; and
   c) a readily removable member disposed along said outer sheath along at least a portion of said load area, said readily removable member having a semi-tubular configuration with a substantially U-shaped cross section and having sufficient rigidity to substantially prevent said outer sheath from expanding along said load area prior to delivery of said self-expanding stent.

13. A delivery apparatus for a self-expanding stent, said apparatus comprising:
   a) an outer sheath, comprising an elongated tubular member having distal and proximal ends, an inner shaft located coaxially within said outer sheath, said inner shaft having a distal end, extending distal to said distal end of said outer sheath, and a proximal end, extending proximal to said proximal end of said outer sheath, said inner shaft further including a stop attached thereto, said stop being proximal to said distal end of said outer sheath;
   b) a self expanding stent located within said outer sheath, said self-expanding stent making frictional contact with an inner layer of said outer sheath along a load area, said load area located between said stop and said distal end of said outer sheath with a portion of said inner shaft disposed coaxially within a lumen of said self-expanding stent; and c) a readily removable member disposed along said outer sheath along at least a portion of said load area, said readily removable member having a semi-tubular configuration with a substantially U-shaped cross section and having sufficient rigidity to substantially prevent said outer sheath from expanding along said load area prior to delivery of said self-expanding stent.

14. A delivery apparatus for a self-expanding stent, said apparatus comprising:

a) an outer sheath comprising an elongated tubular member having distal and proximal ends and an inside and outside diameter, said outer sheath having an enlarged section at its distal end, said enlarged section having a greater inside and outside diameter than said inside and outside diameter of said outer sheath proximal to said enlarged section;

b) an inner shaft located coaxially within said outer sheath, said inner shaft having a distal end and a proximal end, said inner shaft further including a stop attached thereto, said stop being proximal to said distal end of said outer sheath; and c) a self-expanding stent located within said enlarged section of said outer sheath, said self-expanding stent making frictional contact with said outer sheath along a load area, said inner shaft disposed coaxially within a lumen of said self-expanding stent; and d) a readily removable member disposed along said outer sheath along at least a portion of said load area, said readily removable member having a semi-tubular configuration with a substantially U-shaped cross section and having sufficient rigidity to substantially prevent said outer sheath from expanding along said load area prior to delivery of said self-expanding stent.

15. A delivery apparatus for a self-expanding stent, said apparatus comprising:

a) an outer sheath comprising an elongated tubular member having distal and proximal ends and an inside and outside diameter, said outer sheath having an enlarged section at its distal end, said enlarged section having a greater inside and outside diameter than said inside and outside diameter of said outer sheath proximal to said enlarged section;

b) an inner shaft located coaxially within said outer sheath, said inner shaft having a distal end and a proximal end, said inner shaft further including a stop attached thereto, said stop being proximal to said distal end of said outer sheath; and c) a self-expanding stent located within said enlarged section of said outer sheath, said self-expanding stent making frictional contact with said outer sheath along a load area, said inner shaft disposed coaxially within a lumen of said self-expanding stent; and d) a readily removable member disposed along said outer sheath along at least a portion of said load area, said readily removable member having a semi-tubular configuration with a substantially C-shaped cross section and having sufficient rigidity to substantially prevent said outer sheath from expanding along said load area prior to delivery of said self-expanding stent.

* * * * *